United States Patent
Iwamoto et al.

(10) Patent No.: US 8,206,567 B2
(45) Date of Patent: *Jun. 26, 2012

(54) REFERENCE ELECTRODE WITH NON-BLOCKING LIQUID JUNCTION

(75) Inventors: Yasukazu Iwamoto, Kyoto (JP); Naomi Kitaoka, Kyoto (JP)

(73) Assignee: Horiba, Ltd., Kyoto (JP)

( * ) Notice: Subject to any disclaimer, the term of this patent is extended or adjusted under 35 U.S.C. 154(b) by 959 days.

This patent is subject to a terminal disclaimer.

(21) Appl. No.: 11/832,537

(22) Filed: Aug. 1, 2007

(65) Prior Publication Data

US 2008/0011607 A1    Jan. 17, 2008

Related U.S. Application Data

(63) Continuation of application No. 10/384,209, filed on Mar. 7, 2003, now Pat. No. 7,264,701.

(30) Foreign Application Priority Data

Mar. 8, 2002 (JP) .................. 2002-064134

(51) Int. Cl.
*G01N 27/40* (2006.01)
(52) U.S. Cl. ............ 204/435; 204/419; 205/792.5
(58) Field of Classification Search ............ 204/419, 204/435; 205/792.5
See application file for complete search history.

(56) References Cited

U.S. PATENT DOCUMENTS

| | | | | |
|---|---|---|---|---|
| 3,461,055 A | * | 8/1969 | Staunton ............ | 204/435 |
| 3,622,268 A | * | 11/1971 | Wada et al. ............ | 423/24 |
| 3,793,176 A | | 2/1974 | Jerrold-Jones | |
| 4,051,026 A | * | 9/1977 | Cremers et al. ............ | 423/24 |
| 4,209,368 A | | 6/1980 | Coker et al. | |
| 4,401,548 A | | 8/1983 | Brezinski | |
| 4,575,410 A | * | 3/1986 | Neti ............ | 204/422 |
| 4,891,124 A | | 1/1990 | Rigdon et al. | |
| 5,034,113 A | | 7/1991 | Iwamoto | |
| 5,071,537 A | | 12/1991 | Yamaguchi et al. | |
| 5,294,356 A | * | 3/1994 | Tanaka et al. ............ | 508/462 |
| 5,302,274 A | | 4/1994 | Tomantschger et al. | |
| 5,344,548 A | | 9/1994 | Alberti et al. | |
| 5,470,453 A | | 11/1995 | Nipkow et al. | |
| 5,908,400 A | * | 6/1999 | Higo et al. ............ | 604/20 |
| 6,004,442 A | * | 12/1999 | Choulga et al. ............ | 204/416 |
| 6,232,485 B1 | | 5/2001 | Derbyshire et al. | |
| 6,495,012 B1 | | 12/2002 | Fletcher et al. | |

FOREIGN PATENT DOCUMENTS

| | | |
|---|---|---|
| DE | 33 05 962 | 8/1984 |
| JP | 02-107959 | 4/1990 |
| JP | 07-159367 | 6/1995 |

OTHER PUBLICATIONS

Kraus et al, Journal of the American Chemical Society, 78, p. 249, 1956.*
Chokkaram S, et al. Ion Exchange and Thermal Studies of Sulfate Zirconia, Journal of Colloid and Interface Science, Academic Press, New York, NY, vol. 165, No. 1, Jun. 1, 1994, pp. 160-168.
Wang Bingji et al.; Study of New Inorganic Ion Exchangers, I. Synthesis and Properties of Zirconium Vanadoyrophosphate, Engineering Information, Inc., New York, NY, Apr. 1, 1994, XP-002266515; Full English translation.

* cited by examiner

*Primary Examiner* — Kaj K Olsen

(57) ABSTRACT

A reference electrode traps silver ions and chloro complex ions leaching to an internal filling solution so that the blocking of the liquid junction can be prevented. A silver/silver chloride electrode can be provided as an internal electrode in an internal filling solution; and a tube which houses, in order from top to bottom, the internal electrode, an inorganic cation exchanger for trapping silver ions and/or chloro complex ions from leaching from the internal electrode, and a ceramic member for preventing the diffusion of the silver ions and/or the chloro complex ions to the internal filling solution.

19 Claims, 4 Drawing Sheets

REFERENCE ELECTRODE WITH NON-BLOCKING LIQUID JUNCTION

RELATED APPLICATIONS

The present application is a continuation application from U.S. patent application Ser. No. 10/384,209 filed on Mar. 7, 2003 now U.S. Pat. No. 7,246,701.

BACKGROUND OF THE INVENTION

1. Field of the Invention

The present invention relates to a reference electrode having an internal electrode in an internal filling solution, and more particularly to improvements that avoid blocking of a liquid junction.

2. Description of Related Art

When a reference electrode such as a silver/silver chloride is in operation, soluble silver ions ($Ag^+$) can leach from the silver/silver chloride electrode, and dissolved chloro complex ions (such as $AgCl_2^-$) can be formed by the following reactions:

(1)

(2)

If such chloro complex ions meet a low chloride ion water at the liquid junction, a reaction can proceed in the direction from right to left according to each formula above and consequently AgCl (silver chloride) can precipitate at the junction.

Particularly, in any continuous operation at a high temperature of 60° C. or above, the silver ions ($Ag^+$) and the dissolved chloro complex ions (such as $AgCl_2^-$) may increase in concentration, and at a lowered temperature, they can form silver chloride, with which the liquid junction can be blocked. Specifically, in continuous operation at 100° C., the liquid junction can be blocked with silver chloride within several days. Interfering substances such as proteins, silver, mercury, and $H_2S$ contained in liquid analytes can also come through the liquid junction into the internal filling solution. In such a case, they can also cause a displacement of the internal electrode potential or react with the silver ions to form less soluble precipitates with which the liquid junction can be blocked.

Therefore, conventional techniques include periodically replacing the internal filling solution to prevent an increase in the content of the silver or chloro complex ions, and/or forcing the internal filling solution to leak so that intake of the liquid analyte can be prevented under pressure changes caused by thermal cycles.

However, the former conventional technique does not drastically eliminate the silver ion, a liquid junction-blocking factor, and the maintenance thereof is not so easy. The later conventional technique needs a complicated structure of the reference electrode that will cause an increase in cost, and is less effective in continuous operation.

The present invention has been made in light of the above-mentioned problems.

SUMMARY OF THE INVENTION

An object of the present invention is to provide a reference electrode that can trap the silver ions and the chloro complex ions from leaching into the internal filling solution so that any blocking of the liquid junction can be prevented.

A further object is to provide a reference electrode having an internal electrode, an internal filling liquid and an inorganic cation exchanger positioned between the internal electrode and the internal filing liquid to prevent diffusion of ions from the internal electrode to the internal filling liquid.

A still further object is to provide one or more porous ceramic members between the reference electrode and the internal filing liquid to block ions.

Another object is to provide a particulate inorganic cation exchanger as an additive to the internal filling fluid.

In order to achieve these objects, the reference electrode according to the present invention can include a silver/silver chloride electrode as an internal electrode provided in an internal filling solution; and a tube which houses, in order from top to bottom, the internal electrode, an inorganic cation exchanger for trapping silver ions and/or chloro complex ions leaching from the internal electrode, and a ceramic member for preventing the diffusion of the silver ions and/or the chloro complex ions to the internal filling solution, wherein the tube is immersed in the internal filling solution.

Specifically, for example, between the internal electrode and the inorganic cation exchanger, the tube may house another ceramic member for inhibiting the leaching of the silver ions and/or the chloro complex ions from the internal electrode to the inorganic cation exchanger.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

The following description is provided to enable any person skilled in the reference electrode art to make and use the invention and sets forth the best modes contemplated by the inventors of carrying out their invention. Various modifications, however, will remain readily apparent to those skilled in the art, since the general principles of the present invention have been defined herein specifically to provide an improved reference electrode that addresses blockage of the liquid junction.

The present invention is now described in detail with references to the drawings.

Figure 1:
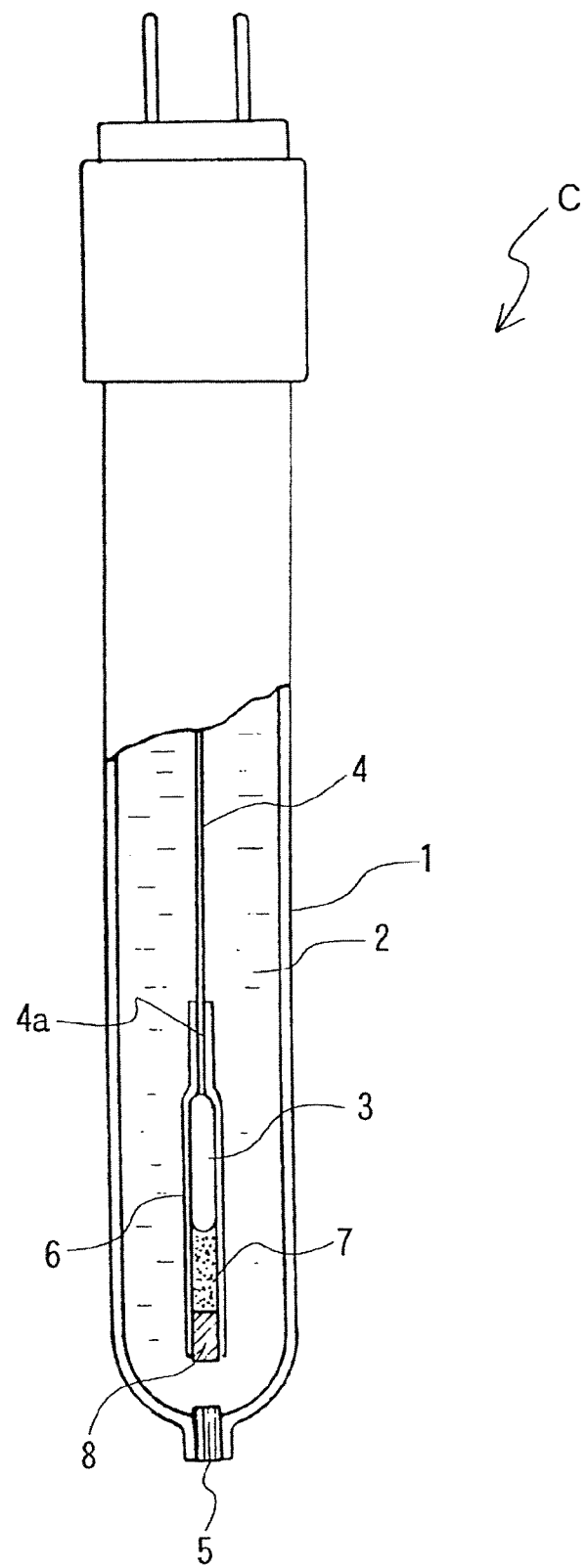
FIG. 1 is a partial view showing a structure of a first embodiment according to the present invention.

FIG. 1 shows a first embodiment according to the present invention including a tube which houses, in the order from top to bottom, an internal silver/silver chloride electrode, an inorganic cation exchanger, and a ceramic member, wherein the tube is immersed in an internal filling solution.

In FIG. 1, numeral 1 represents an outer tube of a reference electrode C, which is formed of a tube-shaped material such as glass tubing. Numeral 2 represents an internal filling solution such as a KCl solution charged in the outer tube 1. Numeral 3 represents an internal electrode such as a silver/silver chloride electrode having a part of a silver rod 4 and silver chloride which has been attached to a tip A of the silver rod in a fused state. The internal electrode 3 can be housed in an inner tube 6 as described below.

Numeral 5 represents a liquid junction that is provided at a lower end of the tube 1 and can be made of a material such as a ceramic. Examples of ceramic include $(SiO_2+Al_2O_3)$ based ceramics and $ZrO_2$ based ceramics.

Numeral 6 represents an inner tube immersed in the internal filling solution 2. The inner tube 6 houses, in order from top to bottom, the internal silver/silver chloride electrode 3, an inorganic cation exchanger 7, and a ceramic member 8 for preventing the diffusion of silver ions $(Ag^+)$ and chloro complex ions (such as $AgCl_2^-$) to the internal filling solution 2. The inorganic cation exchanger 7 has the function of trapping the silver ions $(Ag^+)$ and the dissolved chloro complex ions (such as $AgCl_2^-$) that may leach from the internal electrode 3.

The ceramic member 8, which differs from the liquid junction 5 in material, has the function of preventing the diffusion of the silver ions $(Ag^+)$ and the dissolved chloro complex ions (such as $AgCl_2^-$) from the internal electrode 3 to the internal filling solution 2. For example, the ceramic member 8 can be made of a porous ceramic preferably porous $Al_2O_3$ ceramic with a pore size of several μm to several tenths of μm.

For example, a $ZrO_2$ based cation exchanger manufactured by Toagosei Co., Ltd. as a particulate in a powder size within the range of 1 μm to 100 μm and distributed under the trade name IXE can be used as the inorganic cation exchanger 7.

In this embodiment, the inner tube 6 is formed of heat shrinkable tube preferably a polyolefine based heat-shrinkable tube. An adhesive is applied on the inner surface of the inner tube 6 so that in an upper place of the inner tube 6, a lower end portion 4a of the silver rod 4 and the internal electrode 3 extending therefrom in a lower direction are housed in a well-sealed manner. Preferred adhesives include polyimides.

In a lower place of the inner tube 6, the ceramic member 8 is also housed in a well-sealed manner.

In an intermediate place of the inner tube 6, the inorganic cation exchanger 7 is sandwiched between the internal electrode 3 at an upper position and the ceramic member 8 at a lower position and housed in a well sealed manner.

In this structure, the silver ions $(Ag^+)$ and the dissolved chloro complex ions (such as $AgCl_2^-$) leaching from the internal electrode 3 are trapped by the inorganic cation exchanger 7 so that the generation of silver chloride can be prevented. The electrode potential can also be free from the influence which would otherwise be caused by deposition of silver chloride on the liquid junction 5. In addition, the ceramic member 8 when placed under the inorganic cation exchanger 7 can prevent the diffusion of the silver ions $(Ag^+)$ and the dissolved chloro complex ions (such as $AgCl_2^-$) from migrating to the internal filling solution 2.

Figure 3:
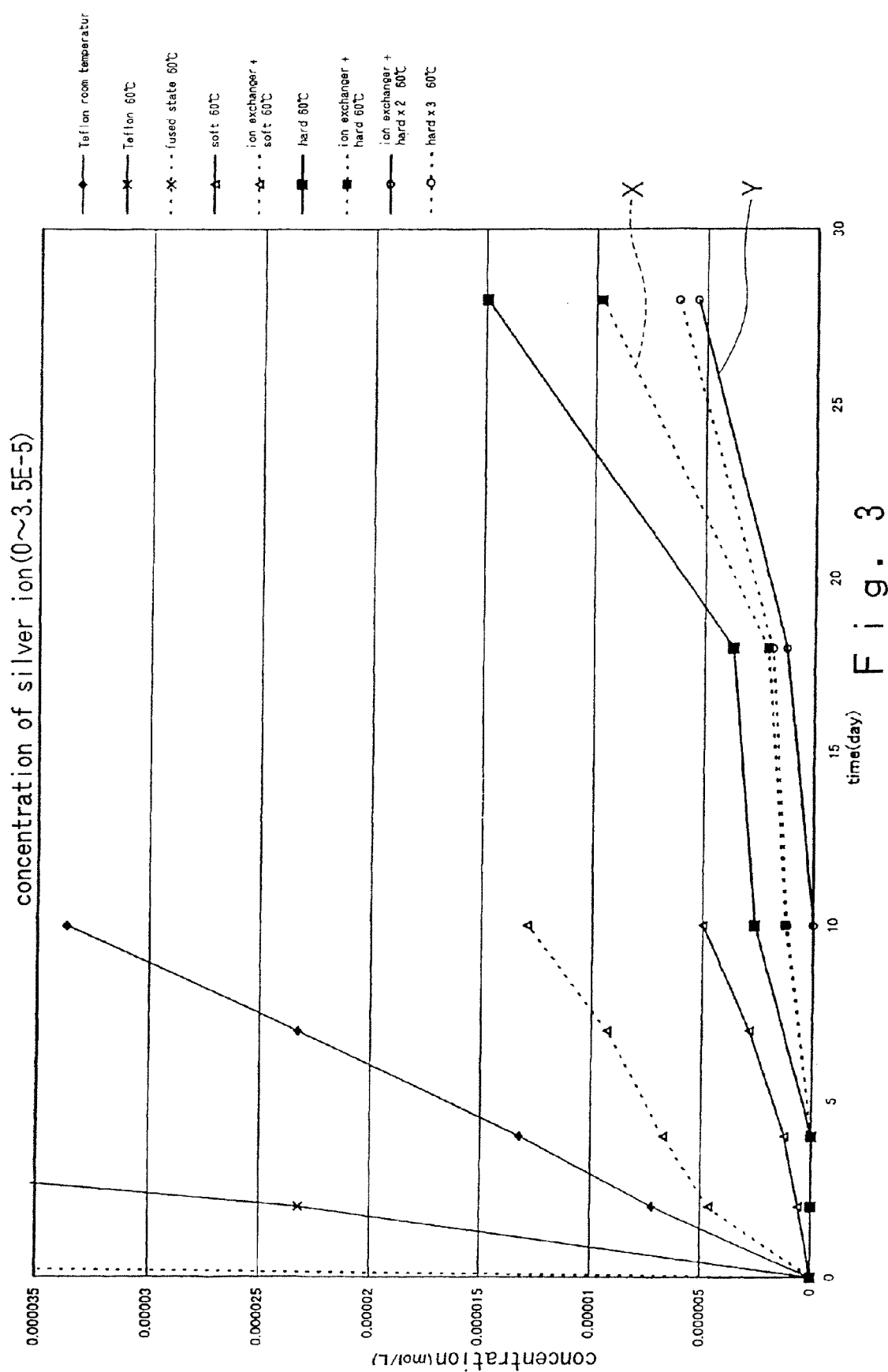
FIG. 3 is a chart diagram showing the effects of the present invention.

From a characteristic line indicated with X in FIG. 3, it can be understood that the generation of chloride ions in the liquid junction 5 is inhibited by the structure having the inorganic cation exchanger 7 at the lowermost part of the internal electrode 3 in contrast with those conventional examples each having only a Teflon (Registered trademark) coating on the internal silver chloride electrode. In FIG. 3, the ordinate axis represent the concentration of the silver ion in the internal filling solution 2.

Figure 2:
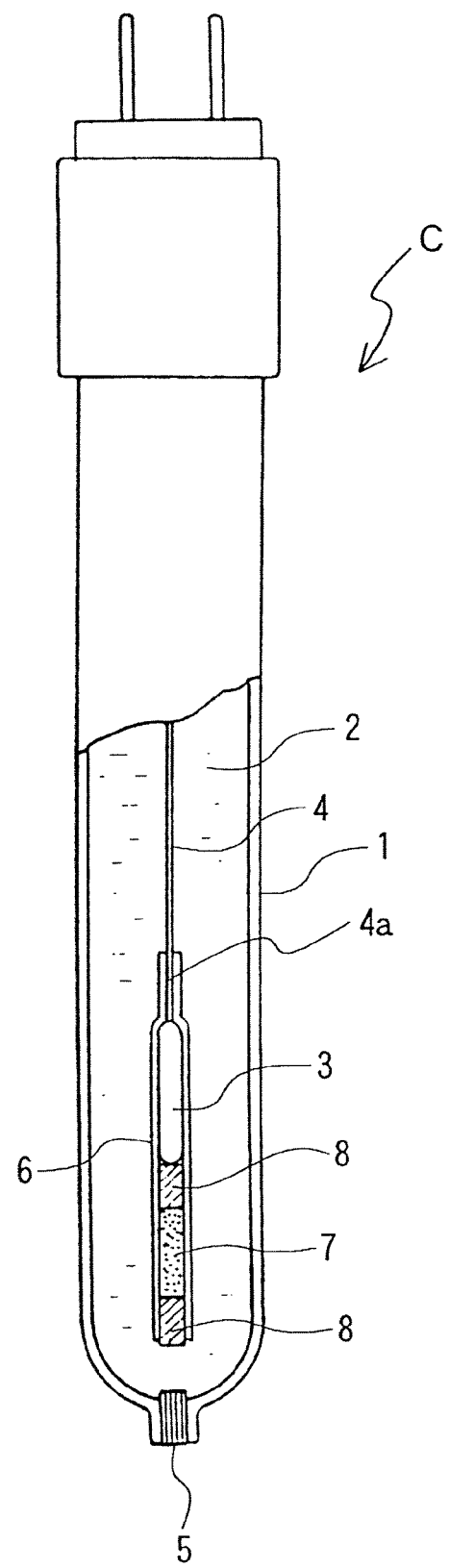
FIG. 2 is a partial view showing a structure of a second embodiment according to the present invention.

FIG. 2 shows a second embodiment according to the present invention including an inner tube 6 which houses, in order from top to bottom, an internal silver/silver chloride electrode 3; a ceramic member 8 for immediately blocking silver ions $(Ag^+)$ and chloro complex ions (such as $AgCl_2^-$) leaching from the internal electrode 3 to an inorganic cation exchanger 7; the inorganic cation exchanger 7 for trapping the silver ions $(Ag^+)$ and the dissolved chloro complex ions (such as $AgCl_2^-$) each leaching from the internal electrode 3; and a ceramic member 8 for preventing the diffusion of the silver ions $(Ag^+)$ and the chloro complex ions (such as $AgCl_2^-$) from the internal electrode 3 to the internal filling solution 2, wherein the inner tube 6 is immersed in the internal filling solution 2. In FIGS. 1 and 2, the same numerals represent the same or corresponding elements.

In this embodiment, the inorganic cation exchanger 7 is sandwiched between the two ceramic members 8 and 8 placed at the upper and lower positions, respectively. In such a structure, the electrode potential can be more reliably freed from an influence which would otherwise be caused by deposition of silver chloride on the liquid junction 5.

The ceramic member 8 provided between the internal electrode 3 and the inorganic cation exchanger 7 prevents the dissolution (leaching) of the silver ions $(Ag^+)$ and the dissolved chloro complex ions (such as $AgCl_2^-$) into the inorganic cation exchanger 7. Therefore, the ion exchange reaction by the inorganic cation exchanger 7 can be more effective in preventing the release of the ions to the internal filling solution 2.

From the characteristic line indicated with Y in FIG. 3, it can be further understood, that in contrast with the conventional examples each having only a Teflon coating on the internal silver/silver chloride electrode, the diffusion of the silver ions and the dissolved chloro complex ions to the internal filling solution 2 is more effectively suppressed by a structure having the inorganic cation exchanger 7 sandwiched between the two ceramic members 8 and 8, one provided at the lowermost part of the internal electrode 3 to immediately block the silver ions $(Ag^+)$ and the dissolved chloro complex ions (such as $AgCl_2^-$) leaching to the inorganic cation exchanger 7, the other provided at the lowermost part of the inorganic cation exchanger 7 to have the function of preventing the diffusion of the silver ions $(Ag^+)$ and the dissolved chloro complex ions (such as $AgCl_2^-$) from the internal electrode 3 to the internal filling solution 2.

Figure 4:
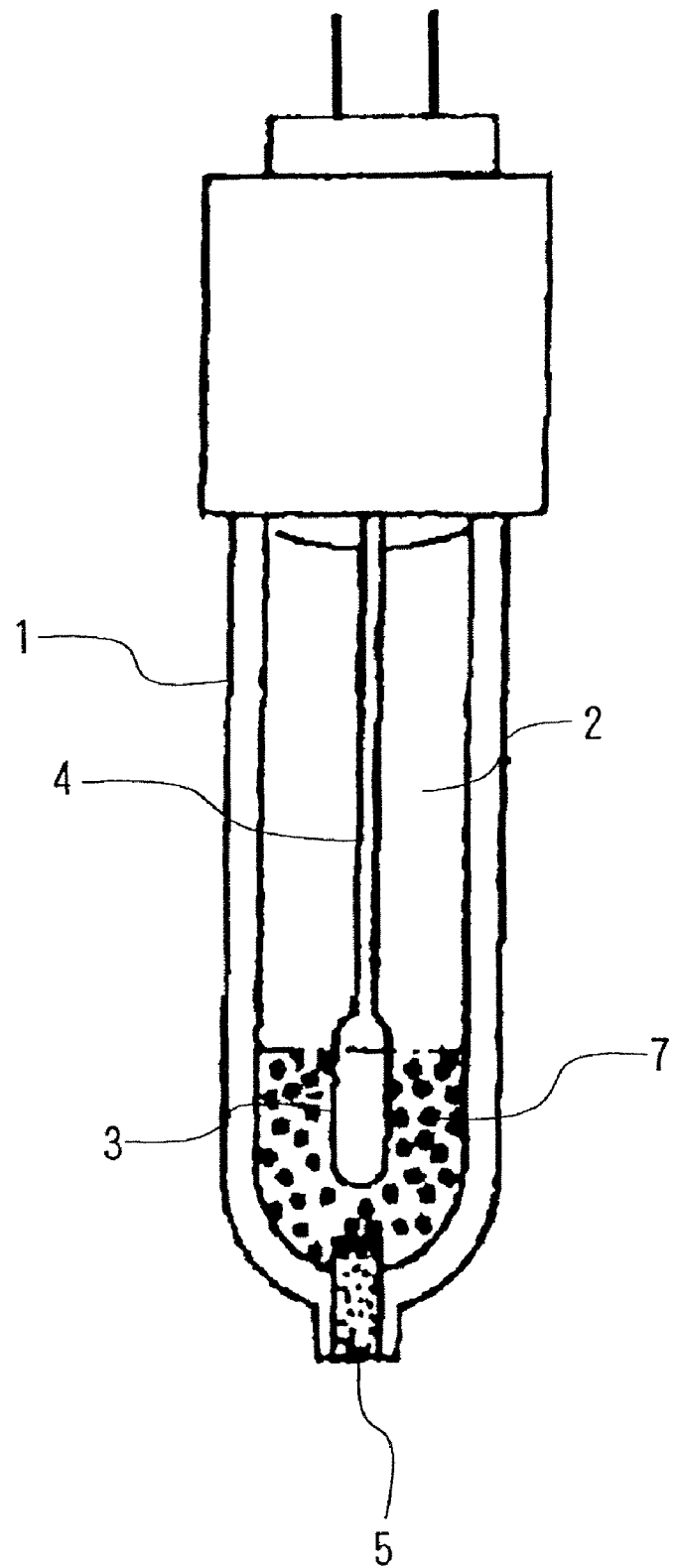
FIG. 4 is a schematic view showing a structure of a third embodiment according to the present invention.

FIG. 4 shows a third embodiment according to the present invention including an inorganic cation exchanger 7 which is provided in an internal filling solution 2 so as to trap silver ions (Ag+) and dissolved chloro complex ions (such as such as $AgCl_2^-$) leaching from an internal electrode 3. In FIGS. 1 to 3, and 4, the same numerals represent the same or corresponding elements.

In this structure, the inorganic cation exchanger 7 is placed over the upper portion of a liquid junction 5. The inorganic cation exchanger 7 may be provided as a particulate additive to the internal filling solution 2 in the amount of 300 to 500 mg to a volume of internal fluid of 5 to 10 ml. The particulate cation exchanger 7 will settle to the bottom of the housing without being required to be fixed in place. This is particularly applicable to reference electrodes that are maintained in a static position.

This embodiment works as follows. As in the case of each embodiment described above, the inorganic cation exchanger 7 traps ions such as silver ions (Ag+) so that the generation of silver chloride in the vicinity of the liquid junction 5 and the blocking thereof can effectively be prevented.

In addition, if the interfering substances such as proteins, silver, mercury, and $H_2S$ come through the liquid junction 5 into the internal filling solution 2, the inorganic cation exchanger 7 can scavenge them. Consequently, the displacement of the electrode potential which would otherwise be caused by the interfering substances can be avoided.

As described above, according to the present invention, the reference electrode includes an internal silver/silver chloride electrode provided in an internal filling solution; and a tube immersed in the internal filling solution, wherein the tube houses, in the order from top to bottom, the internal electrode, an inorganic cation exchanger for trapping silver ions and/or chloro complex ions leaching from the internal electrode, and a ceramic member for preventing the diffusion of the silver ions and/or the chloro complex ions to the internal filling solution.

Between the internal electrode and the inorganic cation exchanger, the tube may also have another ceramic member for blocking the silver ions and/or the chloro complex ions leaching from the internal electrode to the inorganic cation exchanger.

Accordingly, the silver ions and/or the chloro complex ions are trapped by the inorganic cation exchanger, and the diffusion of the silver ions and/or the chloro complex ions to the internal filling solution can immediately be suppressed, so that the generation of silver chloride can be prevented. In addition, the electrode potential can be free from the influence which would otherwise be caused by disposition of silver chloride on the liquid junction.

Those skilled in the art will appreciate that various adaptations and modifications of the just-described preferred embodiments can be reconfigured without departing from the scope and spirit of the invention. Therefore, it is to be understood that, within the scope of the appended claims, the invention may be practiced other than as specifically described herein.

What is claimed is:

1. A reference electrode assembly containing an internal filling solution, comprising:
    an Ag/AgCl internal electrode formed of a silver rod having a lower tip end of AgCl; and
    an inner tube which houses, in order from a top side to a bottom side, the internal electrode, a first ceramic member, an inorganic cation exchanger, of a particulate powder of $ZrO_2$, for trapping any silver ions leaching from the internal electrode, and a second ceramic member for preventing any diffusion of the silver ions to the internal filling solution which includes chloride, wherein said inner tube is immersed in the internal filling solution and seals directly to a side of the lower tip end of AgCl and to sides of the first ceramic member and second ceramic member while permitting access of the second ceramic member to the internal filling solution,
    wherein between the internal electrode and the inorganic cation exchanger, said inner tube houses the first ceramic member for inhibiting any leaching of the silver ions from the internal electrode to the inorganic cation exchanger.

2. The reference electrode assembly of claim 1, wherein said internal electrode is contained and sealed within said inner tube on the top side by an adhesive.

3. The reference electrode assembly of claim 1, wherein said first ceramic member is contained and sealed within said inner tube on the bottom side by an adhesive.

4. The reference electrode assembly of claim 1 wherein the first ceramic member has pore sizes within a range of several μm to 0.1 μm.

5. The reference electrode assembly of claim 4 wherein the second ceramic member is $Al_2O_3$ and the inner tube is sealed to the second ceramic member adjacent a second end of the inner tube to maintain the particulate powder of $ZrO_2$ between the first ceramic member and the second ceramic member.

6. The reference electrode assembly of claim 5, wherein said internal electrode is contained and sealed within a heat-shrinkable inner tube on the top side.

7. The reference electrode assembly of claim 6 wherein a sealing adhesive including a polyimide is provided between the internal electrode and the inner tube.

8. The reference electrode assembly of claim 1 wherein the first and second ceramic members are a porous $Al_2O_3$ ceramic with pore sizes of several μm to several tons of μm and the particulate powder of $ZrO_2$ is captured between the first and second ceramic members.

9. In a reference electrode assembly having an internal electrode of a silver/silver chloride composition, immersed in an internal filling solution and a liquid junction, the internal electrode comprising a first portion and a second portion, the improvement comprising:
    an inner housing having a wall surrounding the internal electrode and sealed to the first portion of the internal electrode at a silver portion by a first end of the inner housing and open at a second end of the inner housing, wherein the inner housing is a plastic tube and the inner housing wall is immersed in the internal filling solution which includes chloride and blocks the internal filling solution egress to the internal electrode to only the open second end of the inner housing;
    an inorganic cation exchanger material positioned adjacent one end of the second portion of the internal electrode located at an edge of an end of the internal electrode within the inner housing such that the inorganic cation exchanger material contacts the internal electrode at the second portion of the internal electrode which is formed of AgCl whereby any dissolved silver ions and chloro complex-ions interacting with the inorganic cation exchanger material are trapped by the inorganic cation exchanger material; and
    a porous ceramic member is sealed to the inner housing between the inorganic cation exchanger material and the second open end, the porous ceramic member prevents diffusion of the silver ions and chloro complex-ions into the internal filling solution, wherein the inorganic cation exchanger material includes $ZrO_2$ in the form of a particulate powder.

10. The reference electrode assembly of claim 9 wherein the porous ceramic member is $Al_2O_3$.

11. The reference electrode assembly of claim 9 wherein pore sizes of the porous ceramic member is within a range of several μm to 0.1 μm.

12. The reference electrode assembly of claim 9 wherein the inner housing is a polyolefin heat-shrinkable tube.

13. The reference electrode assembly of claim 9 has an internal filling solution of KCl.

14. The reference electrode assembly of claim 9 wherein the internal electrode has a rod of silver sealed to the first end of the inner housing and silver chloride is fused to the silver rod and is in contact with the inorganic cation exchanger material.

15. The reference electrode assembly of claim 9 wherein a sealing adhesive is provided between the internal electrode and the inner housing.

16. The reference electrode assembly of claim 9 wherein said internal electrode is contained and sealed within a heat-shrinkable inner housing tube.

17. In a reference electrode assembly having an internal electrode of a silver/silver chloride composition, immersed in an internal filling solution and a liquid junction, comprising a first portion and a second portion of the internal electrode, the improvement comprising:

an inner housing of an elongated tubular configuration surrounding the internal electrode and sealed to the internal electrode at a first end of the inner housing on the first portion of the internal electrode and open at a second end of the inner housing, and the inner housing is immersed in the internal filling solution which includes chloride and blocks the internal filling solution egress to the internal electrode to only the open second end of the inner housing wherein the internal electrode has a rod of silver sealed to the first end of the inner housing at the first portion and silver chloride is fused to the silver rod at a second portion;

an inorganic cation exchanger material positioned adjacent the second portion of the internal electrode located at an edge of an end of the internal electrode within the inner housing such that the inorganic cation exchanger material only contacts the internal electrode at the second portion of the internal electrode whereby any dissolved silver ions and chloro complex-ions interacting with the inorganic cation exchanger material are trapped by the inorganic cation exchanger material, wherein the inorganic cation exchanger is a particulate powder of $ZrO_2$; and a porous ceramic member is sealed to the inner housing between the inorganic cation exchanger material and the second open end, the ceramic member has pore sizes of a dimension for preventing diffusion of the silver ions and chloro complex-ions into the internal filling solution.

18. The reference electrode assembly of claim 17 wherein the porous ceramic member is $Al_2O_3$ with pore sizes of several μm to several tens of μm.

19. The reference electrode assembly of claim 18 wherein the particulate powder of $ZrO_2$ has grain sizes within a size range of 1 μm to 100 μm and a second porous ceramic member of $Al_2O_3$ is sealed to the inner housing to capture the $ZrO_2$ powder between the porous ceramic members.

* * * * *